United States Patent [19]

Göschke et al.

[11] 4,353,918

[45] Oct. 12, 1982

[54] DEXTROROTATORY BICYCLIC THIADIAZA COMPOUNDS AND PHARMACEUTICAL PREPARATIONS CONTAINING THEM

[75] Inventors: Richard Göschke, Bottmingen; Pier G. Ferrini, Binningen, both of Switzerland

[73] Assignee: Ciba-Geigy Corporation, Ardsley, N.Y.

[21] Appl. No.: 219,195

[22] Filed: Dec. 22, 1980

Related U.S. Application Data

[63] Continuation of Ser. No. 108,904, Dec. 31, 1979, abandoned.

[30] Foreign Application Priority Data

Jan. 5, 1979 [CH] Switzerland ............................. 87/79

[51] Int. Cl.³ ........................................... C07D 277/60
[52] U.S. Cl. .................................... 424/270; 548/154
[58] Field of Search ......................... 548/154; 424/270

[56] References Cited

U.S. PATENT DOCUMENTS

| | | | |
|---|---|---|---|
| 3,274,209 | 9/1966 | Herman | 260/306.7 |
| 3,455,924 | 7/1969 | Tednicer | 260/256.4 |
| 4,042,583 | 8/1977 | Ascheson et al. | 542/458 |
| 4,064,260 | 12/1977 | Cherkofsky et al. | 424/270 |
| 4,109,016 | 8/1978 | Mailliet | 424/342 |
| 4,110,460 | 8/1978 | Baetz | 424/270 |
| 4,153,706 | 5/1979 | Bender et al. | 424/270 |
| 4,175,127 | 11/1979 | Bender et al. | 424/263 |

OTHER PUBLICATIONS

C.A. vol. 72, 12645/p (1970).

*Primary Examiner*—Nicholas S. Rizzo
*Attorney, Agent, or Firm*—Michael W. Glynn; Prabodh I. Almaula

[57] ABSTRACT

The invention relates to the dextrorotatory enantiomer of trans-5,6-di-p-methoxyphenyl-2,3,5,6-tetrahydroimidazo[2,1-b]thiazole and its pharmaceutically acceptable salts and to pharmaceutical preparations containing them.

The new compounds have valuable pharmacological properties, especially anti-inflammatory and anti-rheumatic effects.

10 Claims, No Drawings

DEXTROROTATORY BICYCLIC THIADIAZA COMPOUNDS AND PHARMACEUTICAL PREPARATIONS CONTAINING THEM

This is a continuation of application Ser. No. 108,904 filed on Dec. 31, 1979, now abandoned.

The invention relates to the new dextrorotatory enantiomer of trans-5,6-di-p-methoxyphenyl-2,3,5,6-tetrahydroimidazo[2,1-b]thiazole and the salts thereof and also to processes for the manufacture of the mentioned compound and the salts thereof, as well as pharmaceutical preparations containing the mentioned compound and the salts thereof and the use of the mentioned compound and the salts thereof, preferably in the form of pharmaceutical preparations.

Salts of (+)-trans-5,6-di-p-methoxyphenyl-2,3,5,6-tetrahydroimidazo[2,1-b]thiazole are especially the acid addition salts thereof, especially pharmaceutically acceptable non-toxic salts, for example with inorganic acids, such as hydrochloric acid, hydrobromic acid, sulphuric acid and phosphoric acid, or with organic acids, such as aliphatic, cycloaliphatic, cycloaliphatic-aliphatic, aromatic, araliphatic, heterocyclic and heterocyclic-aliphatic carboxylic or sulphonic acids, for example acetic acid, propionic acid, succinic acid, glycolic acid, lactic acid, malic acid, tartaric acid, citric acid, ascorbic acid, maleic acid, phenylacetic acid, benzoic acid, 4-aminobenzoic acid, anthranilic acid, 4-hydroxybenzoic acid, salicylic acid, aminosalicylic acid, embonic acid and nicotinic acid, and also methanesulphonic acid, ethanesulphonic acid, 2-hydroxyethanesulphonic acid, ethylenesulphonic acid, benzenesulphonic acid, p-toluenesulphonic acid, naphthalenesulphonic acid, sulphanilic acid and cyclohexylsulphamic acid.

The compound according to the invention and the salts thereof have valuable pharmacological properties, especially anti-inflammatory and antirheumatic effects, as shown in experiments on animals. For example, in the kaolin paw oedema test on rats [Helv. Physiol. Acta 25,(1967) 156] at a dose, administered perorally, of approximately 10 mg/kg and above and in the turpentine pleuritis test on rats [Helv. Physiol. Acta 26 (1969) 287] at a dose, administered perorally, of from 30 to 100 mg/kg, they exhibit an anti-inflammatory and an anti-exudative effect. They also exhibit an excellent effect in the adjuvant arthritis test on rats [Pharmacology 2 (1969) 288] at a peroral dose of from 10 to 30 mg/kg.

The new compound and the salts thereof also have an analgesic effect, as shown in the phenyl-p-benzoquinone test on mice [Proc. Soc. Exp. Biol. 95 (1957) 729] at doses of from 30 to 100 mg/kg administered perorally.

Mention should also be made of the inhibitory effect of the new compound and the salts thereof on the prostaglandin synthetase in vitro [Prostaglandins 7, 123 (1974)] in concentrations of from 0.05-20 μg/ml. The new compound and the salts thereof also exhibit a valuable antithrombotic effect, namely protection against fatal pulmonary embolism, in rabbits [Pharmacology 14 (1976) 522] in peroral doses of approximately 0.3 mg/kg.

In addition to this, the new compound and the salts thereof exhibit a reinforcing effect in the pertussis oedema test (Agents and Actions, vol. 6, 613, 1976) at from 5-50 mg/kg/rat.

The new compound and the salts thereof are useful as antiphlogistic agents, for example for the treatment of rheumatic and arthritic complaints and other complaints connected with inflammation, especially rheumatic arthritis, or as analgesic agents, for example for the treatment of pain.

The new compound may be manufactured according to methods known per se.

For example, the enantiomeric mixture may be split up into the enantiomers, the dextrorotatory enantiomer may be isolated and, if desired, the resulting free compound can be converted into a salt or a resulting salt can be converted into the free compound or into a different salt.

The enantiomeric mixture is split up in the normal manner, for example by fractional crystallisation from an optically active solvent, by chromatography, especially thin layer chromatography, using an optically active carrier or preferably by forming salts with optically active acids that form salts with trans-5,6-di-p-methoxyphenyl-2,3,5,6-tetrahydroimidazo[2,1-b]thiazole, separating the diastereoisomeric salt mixture into the diastereoisomers on the basis of different physical properties, such as solubility or adsorptive behaviour, for example by fractional crystallisation or chromatography, and liberating the dextrorotatory enantiomer from the corresponding diastereoisomer in the normal manner, for example by treatment with a base, for example by means of sodium bicarbonate.

Optically active acids forming diastereoisomeric salts with trans-5,6-di-p-methoxyphenyl-2,3,5,6-tetrahydroimidazo[2,1-b]thiazole are, for example, optically active organic acids, preferably monocarboxylic acids or dicarboxylic acids having at least one asymmetric carbon atom, or acid esters or acid salts or amides of dicarboxylic acids with alcohols or organic amines that have at least one asymmetric carbon atom, or sulphonic acids having at least one asymmetric carbon atom. Suitable monocarboxylic acids and dicarboxylic acids having at least one asymmetric carbon atom are, for example, camphoric acid, menthoxyacetic acid, malic acid, mandelic acid and, above all, D-tartaric acid and L-tartaric acid and the O-acyl derivatives thereof and also D-glutamic acid and L-glutamic acid and the N-acyl and N-sulphonyl derivatives thereof. O-acyl derivatives of D-tartaric acid or L-tartaric acid are preferably O,O'-diacyl derivatives of the same, for example, those that are derived from aliphatic, cycloaliphatic, cycloaliphatic-aliphatic, araliphatic or, above all, aromatic carboxylic acids. Aliphatic carboxylic acids are, for example, alkanecarboxylic acids and alkanedicarboxylic acids having up to and including 7 carbon atoms, for example acetic acid, propionic acid, acrylic acid and butyric acid. Cycloaliphatic carboxylic acids are, for example, 5-membered to 8-membered cycloalkanecarboxylic acids, for example cyclopentanecarboxylic acid, cyclohexanecarboxylic acid and cycloheptanecarboxylic acid. Correspondingly, cycloaliphatic-aliphatic carboxylic acids are, for example, 5-membered to 8-membered cycloalkylalkanoic acids having up to and including 4 carbon atoms in the side chain, for example cyclopentylacetic acid, cyclohexyl acetic acid and cycloheptylacetic acid. Araliphatic carboxylic acids are, for example, phenylalkanoic acids that have up to and including 4 carbon atoms in the side chain and that are optionally substituted in the phenyl moiety by alkyl having up to and including 4 carbon atoms, such as methyl, alkoxy having up to and including 4 carbon atoms, such as methoxy, halogen of an atomic number of up to and including 35, such as chlorine, and/or nitro, for example phenylacetic acid or 2-phenylpropionic acid optionally substituted as indicated. Aromatic carboxylic acids are, for example, benzoic acids substituted by alkyl having up to and including 4 carbon atoms, such as methyl, alkoxy having up to and including 4 carbon atoms, such as methoxy, halogen of an atomic number of up to and including 35, such as chlorine, and/or nitro. As O,O'-diacyl derivatives of D-tartaric acid and L-tartaric acid there are preferably used the O,O'-di-p-toluoyl derivatives thereof and also the O,O'-dibenzoyl, O,O'-di-o-toluoyl, O,O'-di-m-toluoyl, O,O'-di-p-chlorobenzoyl, O,O'-di-p-nitrobenzoyl or O,O'-di-2,4-dinitrobenzoyl derivatives thereof. N-acyl derivatives of D-glutamic acid or L-glutamic acid are, for example, the lactams thereof, for example D-pyroglutamic acid and L-pyroglutamic acid, or N-acyl derivatives that are derived from aliphatic, cycloaliphatic, cycloaliphatic-aliphatic, araliphatic or aromatic carboxylic acids, preferably from those mentioned above. N-sulphonyl derivatives of D-glutamic acid or L-glutamic acid are preferably those that are derived from aromatic sulphonic acids, for example N-benzenesulphonyl derivatives optionally substituted by alkyl having up to and including 4 carbon atoms, such as methyl, alkoxy having up to and including 4 carbon atoms, such as methoxy, halogen of an atomic number of up to and including 35, such as fluorine, chlorine or bromine, and/or nitro, especially N-benzenesulphonyl, N-p-toluenesulphonyl, p-nitrobenzenesulphonyl, p-bromobenzenesulphonyl or p-fluorobenzenesulphonyl derivatives of D-glutamic acid or L-glutamic acid.

Suitable optically active sulphonic acids are, for example, camphorsulphonic acids, such as camphor-10-sulphonic acid, 3-bromocamphor-3-sulphonic acid, camphor-7-sulphonic acid and 3-bromocamphor-10-sulphonic acid. Alcohols having at least one asymmetric carbon atom are, for example, aliphatic, araliphatic and cycloaliphatic alcohols, for example 1-phenylethanol, borneol, isoborneol and terpineol. Organic amines having at least one asymmetric carbon atom are, for example, cinchonine, cinchonidine, quinine, quinidine, brucine, ephedrine, amphetamine and menthylamine. Suitable dicarboxylic acid components for the formation of acid esters and acid amides or salts are, for example, phthalic acid, succinic acid and the like.

The trans-5,6-di-p-methoxyphenyl-2,3,5,6-tetrahydroimidazo[2,1-b]thiazole to be used as the starting material may be manufactured, for example, by subjecting 2-imino-3-(1,2-di-p-methoxyphenyl-2-hydroxyethyl)-thiazolidine to acid treatment, for example by treating it at room temperature for approximately 20 hours with concentrated suphuric acid or at approximately 80° C. for approximately 3 hours with polyphosphoric acid, and, if necessary, purifying the crude product by recrystallisation from toluene/petroleum ether or by chromatography using silica gel with chloroform/methanol (15:1) as the eluant. The mentioned 2-imino-3-(1,2-di-p-methoxyphenyl-2-hydroxyethyl)-thiazolidine can, for example, be obtained by condensing α-bromodesoxyanisoin with 2-aminothiazoline and reducing the keto group in the resulting 2-imino-3-(1,2-di-p-methoxyphenyl-2-oxo-ethyl)-thiazolidine to form hydroxymethylene, for example by means of sodium borohydride.

The new compound may also be manufactured by cyclising a 2-(2-X-ethylthio)-4,5-di-p-methoxyphenyl-4-imidazoline of appropriate configuration, for example of the (+)-uhreo configuration, in which X represents a reactive esterified hydroxy group, and, if desired, converting the resulting free compound into one of its salts or converting a resulting salt into the free compound or into a different salt.

Reactive esterified hydroxy is especially hydroxy esterified by a strong inorganic acid, for example hydrogen halide, especially hydrogen chloride, or sulphuric acid, or by a strong organic acid, such as by a lower alkanesulphonic acid, for example methanesulphonic acid and ethanesulphonic acid, or by a benzenesulphonic acid optionally substituted by lower alkyl, lower alkoxy or halogen, for example p-toluenesulphonic acid or p-bromobenzenesulphonic acid.

The cyclisation is carried out preferably under conditions for splitting off acids. The operation is effected especially in a low-boiling solvent, such as dimethylformamide, acetone or an alcohol, for example methanol or ethanol, if desired in the presence of a base, for example an inorganic base, such as an alkali metal hydride, hydroxide or carbonate or an alkaline earth metal hydride, hydroxide or carbonate, especially sodium hydride, sodium hydroxide or sodium carbonate, or an organic base, preferably a nitrogen base, such as tri-lower alkylamine, for example trimethylamine, triethylamine, dimethylisopropylamine, or pyridine.

The starting material may be obtained, for example, by reacting (+)-trans-2-mercapto-4,5-di-p-methoxyphenyl-4-imidazoline with an ethylene glycol, in which at least one of the two hydroxy groups is reactively esterified, and then, if necessary, reactively esterifying the second hydroxy group. The reactively esterified hydroxy groups and also the condensation conditions correspond to those mentioned above. In the case of this reaction, it is possible, especially if both hydroxy groups are reactively esterified, to obtain the starting material in situ; this substance can be cyclised without isolation.

The cis-2-mercapto-4,5-di-p-methoxyphenylimidazoline to be used as the starting material may be obtained, for example, by reducing p-anisoindioxime by treating with nascent hydrogen, such as with an alkali metal and an alcohol, for example with sodium and methanol or ethanol, to form D,L-1,2-di-p-methoxyphenylethylenediamine, splitting this up into the antipodes and reacting the enantiomer of the desired configuration with carbon disulphide.

The new compound may also be obtained by cyclising a 2-imino-3-(2-X-1,2-di-p-methoxyphenylethyl)-thiazolidine of suitable configuration, in which X represents, optionally, reactive esterified hydroxy, or a tautomer thereof, and, if desired, converting the resulting free compound into one of its salts or converting a resulting salt into the free compound.

Reactively esterified hydroxy is especially a hydroxy group esterified by a strong inorganic acid, for example hydrogen halide, especially hydrogen chloride, or sulphuric acid, or by a strong organic acid, such as a lower alkanesulphonic acid, for example methanesulphonic acid or ethanesulphonic acid, or a benzenesulphonic acid optionally substituted by lower alkyl, lower alkoxy or halogen, for example p-toluenesulphonic acid or p-bromobenzensulphonic acid. X is, however, especially a free hydroxy group.

The cyclisation is effected in a manner known per se, if necessary in the presence of a condensing agent and-/or while heating, for example at approximately 50° to 150° C., preferably in an inert solvent. Suitable condensing agents are, for starting materials in which X is hydroxy, for example acid condensing agents and, for starting materials in which X is reactive esterified hydroxy, for example basic condensing agents. Acid condensing agents are, for example, strong Lewis acids, for example sulphuric acid or polyphosphoric acid. Basic condensing agents are, for example, inorganic or organic bases, such as sodium or potassium hydroxide, pyridine or diisopropylethylamine. Inert solvents are, for example, acetonitrile or alcohols, for example methanol or ethanol. Accordingly, if X is a free hydroxy group, cyclisation is carried out preferably under conditions for splitting off water, for example at approximately 50° to approximately 150°, and/or in the presence of an acid catalyst, such as sulphuric acid or polyphosphoric acid. The reaction can also be carried out in the presence of a solvent. If X is a reactively esterified hydroxy group cyclisation takes place, for example, in the presence of sodium or potassium hydroxide, pyridine or diisopropylethylamine under conditions for splitting off water, such as by heating, for example at temperatures of from approximately 50° to approximately 150° C., preferably in the presence of a solvent, such as acetonitrile, or an alcohol, for example methanol or ethanol.

IF X is a free hydroxy group, cyclisation takes place preferably under conditions for splitting off water, for example at approximately 50° to approximately 150° C., and/or in the presence of an acid catalyst, such as strong Lewis acids, for example sulphuric acid or polyphosphoric acid. The reaction can also take place in the presence of a solvent. If X is a reactively esterified hydroxy group, cyclisation takes place, for example, in the presence of an inorganic or organic base, such as sodium or potassium hydroxide, pyridine or diisopropylethylamine.

The starting materials may be obtained, for example, by reacting, in a manner known per se, a 2-oxo-1,2-di-p-methoxyphenyl-1-haloethane of suitable configuration with 2-aminothiazoline or the tautomers thereof, isolating the resulting crystalline product, reducing the keto group with a di-metal hydride to form the hydroxy group and separating an optionally obtained diastereoisomeric mixture into its components in the normal manner, for example by fractional crystallisation. If desired, the hydroxy group may then be converted in the normal manner into a reactive ester.

The above-mentioned condensation takes place preferably at a low temperature, such as −20° to +30° C., especially at room temperature, preferably in a solvent, such as acetonitrile or an aromatic hydrocarbon, such as benzene or toluene, or a halogenated aliphatic hydrocarbon, for example chloroform or methylene chloride. The condensation product precipitates after a short period, generally after approximately 15 to 45 minutes, and is then suction-filtered immediately.

The keto group is reduced preferably in solution or suspension in a lower alcohol, such as methanol or ethanol, at a low temperature, i.e. approximately −20° to +20° C. Di-metal hydrides which are used are those that can reduce a keto group, preferably sodium borohydride. The time taken for reduction may be very long, depending on the size of the crystals in the suspension. A time of 2 to approximately 42 hours must be reckoned with.

Owing to the close relationship between the new compound in free form and in the form of its salts, hereinbefore and hereinafter the free compound shall also include the salts thereof, and the salts shall also include the free compound.

The above reactions are carried out in the normal manner in the presence or absence of diluents, condensing agents and/or catalytic agents, if necessary at reduced or elevated temperature, in a closed vessel and/or in an inert gas temperature.

The process also includes those embodiments according to which compounds formed as intermediates are used as starting materials and the remaining reaction steps are carried out using these, or the process is interrupted at any stage; furthermore, starting materials may be used in the form of derivatives or may be formed during the reaction.

The invention also relates to the diastereoisomeric salts, mentioned as intermediates, of the dextrorotatory enantiomers of trans-5,6-di-p-methoxyphenyl-2,3,5,6-tetrahydroimidazo[2,1-b]thiazole with optically active acids, preferably with organic monocarboxylic or dicarboxylic acids having at least one asymmetric carbon atom, for example with D-tartaric acid or L-tartaric acid or the O,O'-diacyl derivatives thereof, especially salts with (+)-di-O,O'-p-toluoyl-D-tartaric acid and (−)-di-p-toluoyl-L-tartaric acid.

In the biological test arrangements defined initially they have approximately the same effect as the free base or the acid addition salts thereof mentioned initially and they may be used as anti-inflammatory agents, for example for the treatment of rheumatic arthritis.

The new compounds of the present invention may be used, for example, for the manufacture of pharmaceutical preparations that contain an effective quantity of the active substance together or in admixture with inorganic or organic, solid or liquid, pharmaceutically acceptable carriers suitable for enteral or parenteral administration. Thus, tablets or gelatine capsules are used which contain the active substance together with diluents, for example lactose, dextrose, sucrose, mannitol, sorbitol, cellulose and/or glycerine, and lubricants, for example silica, talcum, stearic acid or salts thereof, such as magnesium stearate or calcium stearate, and/or polyethylene glycol; tablets also contain binders, for example magnesium aluminium silicate, starches, such as maize starch, wheat starch, rice starch, or arrowroot starch, gelatine, tragacanth, methylcellulose, sodium carboxymethylcellulose and/or polyvinylpyrrolidone, and, if desired, disintegrating agents, for example starches, agar, alginic acid or a salt thereof, such as sodium alginate, and/or effervescing mixtures, or adsorptive agents, dyestuffs, flavouring substances and sweeteners. Furthermore, the new pharmacologically active compounds may be used in the form of injectable, for example intravenously administrable, preparations or in the form of infusion solutions. Such solutions are preferaby isotonic aqueous solutions or suspensions, it being possible to manufacture these immediately before use, for example from lyophilised preparations that contain the active substance alone or together with a carrier, for example mannitol. The pharmaceutical preparations may be sterilised and/or contain auxiliaries, for example preservatives, stabilisers, wetting agents and/or emulsifiers, solubilisers, salts for regulating the osmotic pressure and/or buffers. The pharmaceutical preparations of the present invention, which, if desired, may contain other pharmacologically valuable substances, are manufactured in a manner known per se, for example by means of conventional mixing, granulating, dragée-making, dissolving or lyophilising processes and contain from approximately 0.1% to 100%, especially from approximately 1% to approximately 50%, or, in the case of lyophilisates, up to 100%, of the active substance. The individual dose for a warm-blooded animal weighing approximately 70 kg is between 0.1 and 0.75 g and the daily dose is between 0.2 and 1.0 g.

The following Examples illustrate the invention; temperatures are given in degrees Centigrade.

EXAMPLE 1

A suspension of 7 ml of 1,2-dibromoethane, 7 g of sodium carbonate and 55 ml of isopropanol is stirred at room temperature and a suspension of 4.7 g of trans-4,5-di-p-methoxyphenylimidazolidine-2-thione in 110 ml of 1.5% sodium hydroxide solution is added in the course of one hour. The reaction mixture is refluxed for 7 hours, then the isopropanol and the dibromoethane are removed using a rotary evaporator and the remaining suspension is extracted with toluene. The toluene extract is washed with brine, dried over sodium sulphate and concentrated by evaporation. The residue is chromatographed on silica gel. After separating non-polar impurities with ethyl acetate, trans-5,6-di-p-methoxyphenyl-2,3,5,6-tetrahydroimidazo[2,1-b]thiazole is eluted in the form of a colourless oil using a mixture of ethyl acetate/methanol (99:1). It crystallises spontaneously to form white crystals having a melting point of 125°–126°.

For further purification the material is divided between ethyl acetate and 2 N hydrochloric acid. The acid phases are adjusted to a pH of 8 with N sodium bicarbonate and extracted with ethyl acetate. After drying and concentrating by evaporation, the residue is recrystallised from toluene/petroleum ether or chromatographed on silica gel using chloroform/methanol (15:1) as the eluant.

The starting material may be manufactured, for example, as follows:

67.7 g of D,L-1,2-di-p-methoxyphenylethylenediamine, obtainable by reducing p-anisoindioxime with sodium in ethanol, are dissolved in 1400 ml of ethanol, 27 g of carbon disulphide are added and the mixture is refluxed for 16 hours. The precipitated crystals are suction-filtered, suspended in 1200 ml of ethanol and refluxed until no more hydrogen sulphide evolves (approximately 30 hours). Trans-4,5-di-p-methoxyphenylimidazolidine-2-thione is obtained and can be used without further purification.

EXAMPLE 2

6.8 g of trans-5,6-di-p-methoxyphenyl-2,3,5,6-tetrahydroimidazo[2,1-b]thiazole are dissolved in 80 ml of chloroform and added to a solution of 8.1 g of (+)-di-O,O'-p-toluoyl-D-tartaric acid in 80 ml of chloroform. The mixture is evaporated to dryness using a rotary evaporator at 50° and the residue is taken up in 50 ml of warm acetone, stirred at room temperature and left to stand for 4 hours. The precipitated crystals are filtered off and then washed with acetone.

Combined with the washing solution, the filtrate is evaporated to dryness under reduced pressure; the oily residue is dissolved in 20 ml of warm acetone and left to stand overnight in a refrigerator. The crystals are collected and recrystallised again from acetone. The di-p-toluoyl-D-tartrate of the (+)-enantiomer of trans-5,6-di-p-methoxyphenyl-2,3,5,6-tetrahydroimidazo[2,1-b]thiazole is obtained having a melting point of 118°–120°, $[\alpha]_D^{20°} = +162°$.

EXAMPLE 3

11.0 g of trans-5,6-di-p-methoxyphenyl-2,3,5,6-tetrahydroimidazo[2,1-b]thiazole are dissolved in 120 ml of chloroform and added to a solution of 13.1 g of (−)-di-O,O'-p-toluoyl-L-tartaric acid in 120 ml of chloroform. The mixture is evaporated to dryness using a rotary evaporator at 50°; the oily residue is taken up in 80 ml of acetone while heating and is left to stand at room temperature for 4 hours. The precipitated crystals are suction-filtered, then washed with acetone and dried at 70° under reduced pressure. The di-p-toluoyl-L-tartrate of the (+)-enantiomer of trans-5,6-di-p-methoxyphenyl-2,3,5,6-tetrahydroimidazo[2,1-b]thiazole is obtained. Melting point 125°–128°, $[\alpha]_D^{20°} = +7°$.

EXAMPLE 4

17.0 g of trans-5,6-di-p-methoxyphenyl-2,3,5,6-tetrahydroimidazo[2,1-b]thiazole are dissolved in 100 ml of warm acetone. Likewise, 7.5 g of L-(+)-tartaric acid are dissolved in 150 ml of warm acetone. After cooling the solutions to room temperature, they are combined, a sticky precipitate being formed. Heating is then effected slowly until the precipitate dissolves. The whole is then allowed to cool slowly with occasional shaking until crystallisation takes place and is left to stand for 3.5 hours at room temperature. The precipitated crystals are separated by decantation and then washed with acetone.

The crystals are dissolved in a total of 500 ml of boiling acetone and the solution is concentrated at boiling temperature to 250 ml. It is then allowed to cool slowly to room temperature, is suction-filtered, washed with a little acetone and allowed to dry under reduced pressure at 60°. The L-(+)-tartrate of the (+)-enantiomer of trans-5,6-di-p-methoxyphenyl-2,3,5,6-tetrahydroimidazo[2,1-b]thiazole is obtained having a melting point of 122°–124°, $[\alpha]_D^{20°} = +116°$.

EXAMPLE 5

9.3 g of the L-(+)-tartrate of the (+)-enantiomer of trans-5,6-di-p-methoxyphenyl-2,3,5,6-tetrahydroimidazo[2,1-b]thiazole are dissolved in 35 ml of water of room temperature and 60 ml of N aqueous sodium bicarbonate solution are added. Extraction is effected twice with ether; the ether extracts are washed with water, dried over sodium sulphate, filtered and concentrated by evaporation. In this manner, the (+)-enantiomer of trans-5,6-di-p-methoxyphenyl-2,3,5,6-tetrahydroimidazo[2,1-b]-thiazole is obtained with $[\alpha]_D^{20°} = +45°$.

EXAMPLE 6

3.6 g of the (+)-enantiomer of trans-5,6-di-p-methoxyphenyl-2,3,5,6-tetrahydroimidazo-[2,1-b]thiazole are dissolved in 40 ml of acetone and added to a solution of 1.55 g of L-(+)-tartaric acid in 150 ml of acetone. The whole is concentrated to approximately 60 ml. The slowly precipitating crystals are suction-filtered after 15 hours, washed with acetone and dried under a high vacuum at 80°. In this manner, the L-(+)-tartrate of the (+)-enantiomer of trans-5,6-di-p-methoxyphenyl-2,3,5,6-tetrahydroimidazo[2,1-b]thiazole is obtained having a melting point of 123°–127°, $[\alpha]_D^{20°} = +114°$.

EXAMPLE 7

Tablets, containing 25 mg of active substance, for example (+)-trans-5,6-di-p-methoxyphenyl-2,3,5,6-tetrahydroimidazo[2,1-b]thiazole may be manufactured in the following manner:

| Ingredients (for 1000 tablets) | |
|---|---|
| active substance | 25.0 g |
| lactose | 100.7 g |
| wheat starch | 7.5 g |
| polyethylene glycol 6000 | 5.0 g |
| talcum | 5.0 g |
| magnesium stearate | 1.8 g |
| demineralised water | q.s. |

Manufacture

All the solid ingredients are first put through a sieve having a mesh width of 0.6 mm. The active substance, the lactose, the talcum, the magnesium stearate and half of the starch are then mixed. The other half of the starch is suspended in 40 ml of water and this suspension is added to a boiling solution of the polyethylene glycol in 100 ml of water. The starch paste obtained is added to the main mixture and the whole is granulated, if necessary with the addition of water. The granulate is dried overnight at 35°, put through a sieve having a mesh width of 1.2 mm and compressed to form tablets approximately 6 mm in diameter that are concave on both sides.

Tablets, each containing 25 mg of a different compound from among those mentioned in Examples 1 to 6 may be manufactured in an analogous manner.

EXAMPLE 8

Chewing tablets, containing 30 mg of active substance, for example (+)-trans-5,6-di-p-methoxyphenyl-2,3,5,6-tetrahydroimidazo[2,1-b]thiazole, may be manufactured, for example, in the following manner:

| Composition (for 1000 tablets): | |
|---|---|
| active substance | 30.0 g |
| mannitol | 267.0 g |
| lactose | 179.5 g |
| talcum | 20.0 g |
| glycine | 12.5 g |
| stearic acid | 10.0 g |
| saccharin | 1.0 g |
| 5% gelatine solution | q.s. |

Manufacture

All the solid ingredients are first put through a sieve having a mesh width of 0.25 mm. The mannitol and the lactose are mixed, granulated with the addition of the gelatine solution, put through a sieve having a mesh width of 2 mm, dried at 50° and put through a sieve again having a mesh width of 1.7 mm. The active substance, the glycine and the saccharin are carefully mixed and the mannitol, the lactose granulate, the stearic acid and the talcum are added. The whole is mixed thoroughly and compressed to form tablets approximately 10 mm in diameter that are concave on both sides and have a score line on the upper side.

Chewing tablets, each containing 30 mg of a different compound from among those mentioned in Examples 1 to 6, may be manufactured in an analogous manner.

EXAMPLE 9

Tablets containing 100 mg of active substance, for example (+)-trans-5,6-di-p-methoxyphenyl-2,3,5,6-tetrahydroimidazo-[2,1-b]thiazole, may be manufactured in the following manner:

| Composition (for 1000 tablets): | |
|---|---|
| active substance | 100.0 g |
| lactose | 248.5 g |
| maize starch | 17.5 g |
| polyethylene glycol 6000 | 5.0 g |
| talcum | 15.0 g |
| magnesium stearate | 4.0 g |
| demineralised water | q.s. |

Manufacture

The solid ingredients are first put through a sieve having a mesh width of 0.6 mm. The active substance, the lactose, talcum, magnesium stearate and half of the starch are then intimately mixed. The other half of the starch is suspended in 65 ml of water and this suspension is added to a boiling solution of the polyethylene glycol in 260 ml of water. The resulting paste is added to the pulverulent substances, the whole is mixed and granulated, if necessary with the addition of water. The granulate is dried overnight at 35°, put through a sieve having a mesh width of 1.2 mm and compressed to form tablets approximately 10 mm in diameter which are concave on both sides and have a score line on the upper side.

Tablets containing 100 mg of a different compound according to one of Examples 1 to 6 may be manufactured in an analogous manner.

We claim:

1. The dextrorotatory enantiomer of trans-5,6-di-p-methoxyphenyl-2,3,5,6-tetrahydroimidazo[2,1-b]thiazole or a pharmaceutically acceptable non-toxic acid addition salt thereof.

2. A compound as claimed in claim 1 being the dextrorotatory enantiomer of trans-5,6-di-p-methoxyphenyl-2,3,5,6-tetrahydroimidazo[2,1-b]thiazole in free form.

3. A compound as claimed in claim 1 being the dextrorotory enantiomer of trans-5,6-di-p-methoxyphenyl-2,3,5,6-tetrahydroimidazo[2,1-b]thiazole in the form of a pharmaceutically acceptable salt with an inorganic or organic acid.

4. A compound as claimed in claim 1 being the dextrorotory enantiomer of trans-5,6-di-p-methoxyphenyl-2,3,5,6-tetrahydroimidazo[2,1-b]thiazole in the form of the hydrochloric acid salt, the hydrobromic acid salt, the sulphuric acid salt or the phosphoric acid salt.

5. A compound as claimed in claim 1 being the dextrorotatory enantiomer of trans-5,6-di-p-methoxyphenyl-2,3,5,6-tetrahydroimidazo[2,1-b]thiazole in the form of a salt with D-tartaric acid or L-tartaric acid or in the form of an O,O'-diacyl derivative of the same derived from benzoic acid optionally substituted by $C_1$-$C_4$-alkyl, $C_1$-$C_4$-alkoxy, halogen of an atomic number of up to and including 35 and/or nitro.

6. A compound as claimed in claim 1 being the dextrorotatory enantiomer of trans-5,6-di-p-methoxyphenyl-2,3,5,6-tetrahydroimidazo[2,1-b]thiazole in the form of the salt with acetic acid, propionic acid, succinic acid, glycolic acid, lactic acid, malic acid, tartaric acid, citric acid, ascorbic acid, maleic acid, phenylacetic acid, benzoic acid, 4-aminobenzoic acid, anthranilic acid, 4-hydroxybenzoic acid, salicylic acid, aminosalicylic acid, embonic acid or nicotinic acid, or alternatively with methanesulphonic acid, ethanesulphonic acid, 2-hydroxyethanesulphonic acid, ethylenesulphonic acid, benzenesulphonic acid, p-toluenesulphonic acid, naphthalenesulphonic acid, sulphanilic acid or cyclohexylsulphamic acid.

7. A compound as claimed in claim 1 being the dextrorotatory enantiomer of trans-5,6-di-p-methoxyphenyl-2,3,5,6-tetrahydroimidazo[2,1-b]thiazole in the form of the L-tartrate.

8. A compound as claimed in claim 1 being the dextrorotatory enantiomer of trans-5,6-di-p-methoxyphenyl-2,3,5,6-tetrahydroimidazo[2,1-b]thiazole in the form the di-p-toluoyl-D-tartrate.

9. A compound as claimed in claim 1 being the dextrorotatory enantiomer of trans-5,6-di-p-methoxyphenyl-2,3,5,6-tetrahydroimidazo[2,1-b]thiazole in the form of the di-p-toluene-L-tartrate.

10. A pharmaceutical preparation having anti-inflammatory and anti-rheumatic action comprising a therapeautically effective amount of a compound of claim 1 and customary pharmaceutical auxiliaries and carriers.

* * * * *